United States Patent
Van Driel et al.

[11] Patent Number: 5,958,167
[45] Date of Patent: Sep. 28, 1999

[54] METHOD OF MAKING TUBING COIL ASSEMBLIES FOR MEDICAL DEVICES

[75] Inventors: Michael R. Van Driel, Fountain Valley; Visith Chung, Chino Hills, both of Calif.

[73] Assignee: Medtronic, Inc., Minneapolis, Minn.

[21] Appl. No.: 08/940,075

[22] Filed: Sep. 29, 1997

[51] Int. Cl.$^6$ ..................................................... B31C 3/16
[52] U.S. Cl. .................. 156/173; 156/272.2; 156/273.7; 264/491
[58] Field of Search ............................... 156/173, 272.2, 156/273.7, 306.3; 264/479, 484, 491, 496, DIG. 40

[56] References Cited

U.S. PATENT DOCUMENTS

| | | | |
|---|---|---|---|
| 4,276,333 | 6/1981 | Cobean | 428/36 |
| 4,419,095 | 12/1983 | Nebergall et al. | 604/96 |
| 4,496,819 | 1/1985 | Acker et al. | 219/769 |
| 5,466,322 | 11/1995 | Munsch | 156/272.2 X |

*Primary Examiner*—Michael W. Ball
*Assistant Examiner*—Shawn A. Mitchell
*Attorney, Agent, or Firm*—Harry G. Weissenberger

[57] ABSTRACT

Coiled medical plastic tubing is set in the coil shape by exposing it to a radio-frequency field while it is subjected to slight radially inward pressure. The amount of pressure and the power of the RF field are so adjusted as to cause the rungs of the coil to lightly stick together without deforming or weakening the coil itself.

6 Claims, 2 Drawing Sheets

METHOD OF MAKING TUBING COIL ASSEMBLIES FOR MEDICAL DEVICES

FIELD OF THE INVENTION

This invention relates to plastic tubing coil assemblies for medical devices or the like, and more particularly to a method of forming and securing tubing coils by radio-frequency energy for improved stability during assembly and shipping.

BACKGROUND OF THE INVENTION

A number of medical devices such as, e.g., hard shell venous reservoirs used in open heart surgery are shipped with plastic tubing which is set into a tight coil for shipment but is pulled into a generally straight configuration (much like the cord on a telephone handset) in use. Typically, the tubing coil is seated in a seating trench in the lid of the reservoir. The coil has a connector on each of its ends, one of which is permanently connected during assembly to a manifold formed on the lid. The other connector is loose, and is connected to other equipment by the user.

The coil is conventionally formed by winding it around a mandrel, and then giving it a permanent set in that form by the application of heat or solvents such as methylethylketone or toluene. Either process not only sets the tubing to its coiled shape but also causes the convolutions of the coil to adhere to each other. This is necessary in order for the coiled tubing to fit exactly into the seating trench, and to resist any axial expansion of the coil during assembly and shipping which would cause it to pop out of the trench. Also, the adhesion of the convolutions allows the end user to pull out only enough convolutions to reach the equipment to which the tubing is to be connected, thereby preventing the tubing from hanging down where it can become entangled or stepped on.

Several problems arise in the fabrication of these tubing coils. One is that the convolutions must stick together enough so that they will not come apart in assembly or shipping, but not so much that they will offer any significant resistance or suffer damage when they are pulled apart by the end user. Both the heating method and the solvent method of setting the coils are deficient in that respect because in both processes, the degree of adhesion of the convolutions is not readily controllable.

A more serious problem arises from the fact that medical equipment is typically manufactured and assembled in a cleanroom. The use of chemical solvents in a cleanroom is highly undesirable because they are usually toxic, corrosive and flammable. The presence of heating elements in the cleanroom is also undesirable because of the presence of isopropyl alcohol fumes which ignite easily due to their low flash point. Heating elements also pose the additional risk of damaging the plastic tubing by melting or burning it if operating parameters are not strictly observed. These factors commonly result in the need to rework 5–10% of the coils in a production setting.

SUMMARY OF THE INVENTION

The present invention solves the above problems of the prior art by giving the coils a permanent set and an accurately controllable adhesion through the use of radio-frequency (RF) energy. In accordance with the invention, the coils are exposed on the mandrel to an RF electric field while being subjected to a light mechanical pressure.

DESCRIPTION OF THE PREFERRED EMBODIMENT

Figure 1:
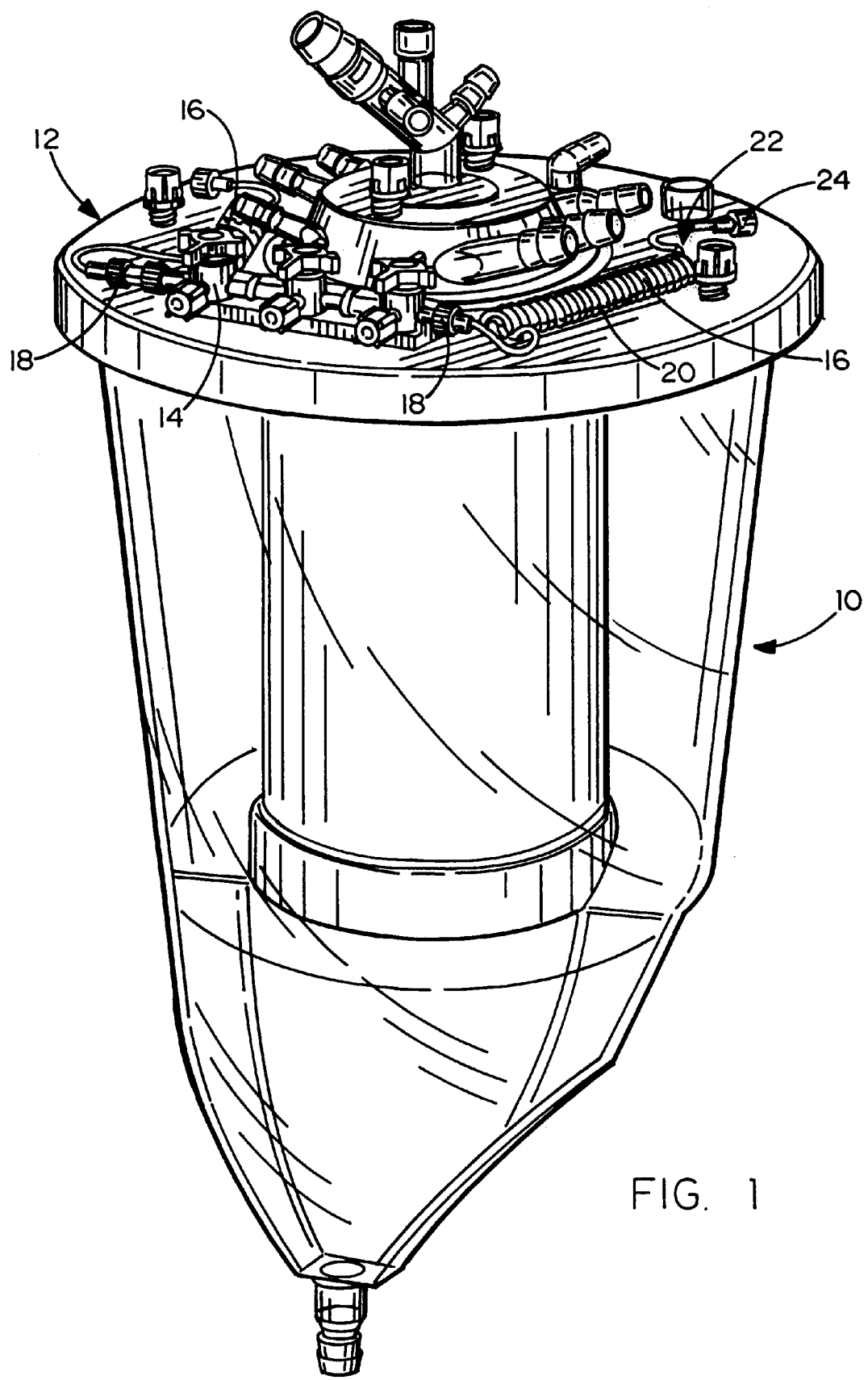
FIG. 1 is a perspective view of a hardshell venous reservoir showing the coil of this invention in shipping position.

FIG. 1 illustrates the environment in which the invention is used. A hardshell venous reservoir 10 associated with a heart-lung machine (not shown) has a lid 12 of rigid plastic material which carries a variety of tubing connectors for a variety of purposes. One of the items carried by the lid 12 is a three-gang stopcock manifold 14 for taking samples of blood from various places in the blood circuit. Each end of the manifold 14 has a coil of polyvinyl chloride (PVC) or silicone tubing 16 connected thereto by a connector 18. The coil 16 rests in a seating trench 20 formed in the lid 12. Its end 22 distal from the manifold 14 is equipped with a connector 24 that can be attached to a selected point in the blood circuit of the heart-lung machine. In order to do this, the perfusionist grasps the connector 24 and pulls out just enough convolutions or rungs of the coil 16 to reach the desired point without having line hanging down or tangling with other lines.

Figure 2:
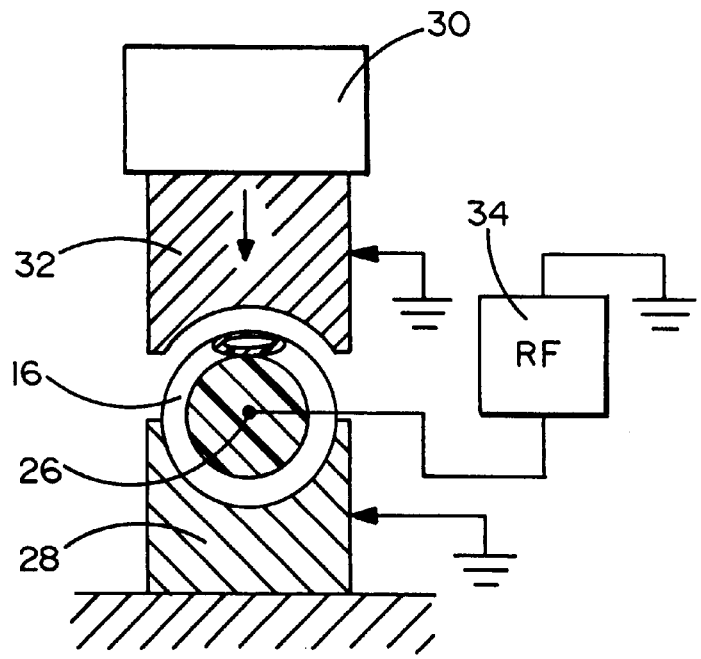
FIG. 2 is a partly schematic vertical transverse section, along line 2—2 of FIG. 3, of the apparatus for forming and setting the coil.
Figure 3:
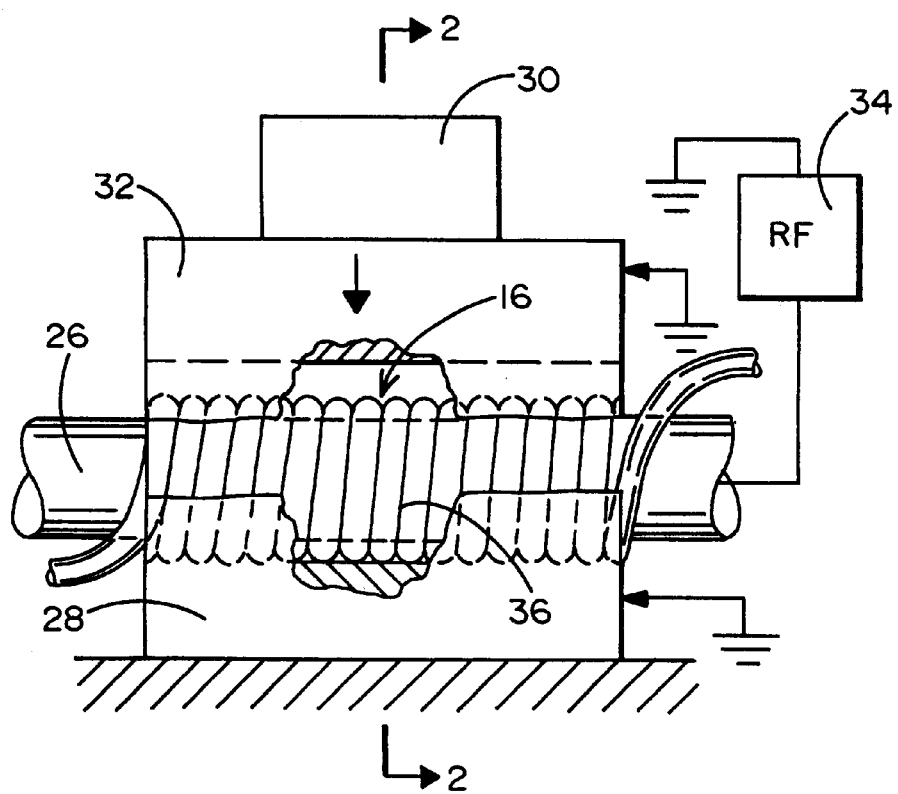
FIG. 3 is a partly schematic vertical axial section of the apparatus of FIG. 2.

FIGS. 2 and 3 illustrate the manufacture of the coils 16. The parameters described below are usable with various types of extended tubing such as PVC, silicone, polyurethane or polyolefin tubing, typically with an inner diameter of 1.6 mm, 3.2 mm or 6.4 mm, and a wall thickness of 0.8 mm, in a coil 16 with a length of about 6 cm. Straight tubing is first tightly wound on a metallic mandrel 26 so that the rungs of the coil 16 lie against each other. While held in that configuration by conventional retaining means (not shown), the coil 16 is placed into the fixed metallic cradle 28 of a press 30. A movable metallic die 32 is then lowered onto the coil 16 to lightly compress it with a pressure of about 0.14–4.76 atmospheres for 2–60 seconds. The cradle 28 and die 32 do not quite touch each other when the die is lowered onto the coil 16.

RF energy from an oscillator 34 is now applied to mandrel 26. The cradle 28 and die 32 are grounded so as to form opposing ground electrodes on each side of the coil 16. The ground electrodes 28 and 32 are preferably semicylindrical in shape and have a diameter substantially equal to the outer diameter of the coil 16. In the axial direction, the electrodes 28 and 32 are preferably of the same length as the coil 16. The applied RF energy preferably has a frequency of about 27 MHz at about 1.5–2 kW for about 2–37 seconds. The above-stated rates provide a choice for the operator: Generally, the lower the pressure, the longer the exposure and dwell times, and vice versa.

The RF circuit establishes an alternating electric field across the coil 16. This field causes an excitation of the molecules of the tubing material, and causes the tubing to set in its coiled shape. The level of RF energy and the applied pressure are not enough to melt, deform or weld the tubing of the coil 16. Nevertheless, particularly with the help of the slight applied pressure, surface molecules of each rung of the coil 16 migrate into the adjacent rung to form a bond 36 which can range in thickness from a molecular level to a few micrometers. This is thick enough to maintain the set of the coil 16 during assembly and shipping, but thin enough to allow easy separation of the rungs without damage to the tubing when the rungs are pulled apart by the end user.

Following the above-described setting operation, the coil 16 can be removed from the mandrel 26 and placed into the seating trench 20 of the lid 12 for connection to the manifold 14 and packaging of the reservoir 10 for shipping.

EXAMPLE

A length of PVC tubing with an inner diameter of 3.18 mm and a wall thickness of 0.76 mm was wound onto a mandrel having a diameter of 10.67 mm and held so that the convolutions or rungs touched each other. Under a die pressure of 4.08 atmospheres, the PVC tubing coil on the mandrel was exposed to 1.6 kW of 27.12 MHz RF energy for 5 seconds, with the pressure maintained for an additional 6 seconds. The press was then opened, and the coil was removed from the mandrel. The coil was found to be set in its coiled shape, with its rungs adhering to each other firmly enough to withstand the imposition of handling and shipping stresses on the coil as a whole, but lightly enough to separate readily when a portion of the coil was pulled in an axial direction. No deformation or weakening of the tubing itself was observed.

The process of this invention differs from conventional flat-plate plastic RF welding, such as that described at pp. 110–112 in the book *Designing Plastic Parts for Assembly* by Paul A. Tres, Hauser/Gardner Publications (1994), in that energy and pressure are kept low enough to lightly adhere the rungs but prevent the local melting of the tubing material. Local melting is essential to welding processes but is undesirable in setting medical tubing because of the danger of producing weak spots or excessive adhesion, or otherwise damaging the tubing. Also, it should be noted that in the inventive process, the pressure is not applied so as to force flat surfaces against each other, but rather to increase molecular mobility in the tubing without deforming it.

It will be understood that the exemplary method of making tubing coils for medical devices described herein and shown in the drawings represents only a presently preferred embodiment of the invention. Indeed, various modifications and additions may be made to such embodiment without departing from the spirit and scope of the invention. Thus, other modifications and additions may be obvious to those skilled in the art and may be implemented to adapt the present invention for use in a variety of different applications.

We claim:

1. A method of setting tubing coils for medical equipment, comprising the steps of:

a) winding plastic tubing into a coil on a mandrel;

b) holding said coil with adjacent convolutions in contact with each other;

c) lightly pressing said coil against said mandrel;

d) subjecting said coil to a radio-frequency electric field while so pressed, said pressing being done at a sufficiently light pressure and said radio-frequency electric field being weak enough to prevent melting of said tubing, but said pressure being sufficient and said field strong enough to cause said adjacent convolutions of said coil to releasably adhere to each other; and e) removing said coil from said mandrel.

2. The method of claim 1, in which said electric field has a frequency of about 27 MHz and a power level of about 1.5–2 kW.

3. The method of claim 1, in which said coil is pressed against said mandrel with a pressure of about 0.14 to 4.76 atmospheres.

4. The method of claim 1, in which said coil is pressed against said mandrel for about 2 to 60 seconds.

5. The method of claim 1, in which said electric field is applied for about 2 to 37 seconds.

6. The method of claim 1, wherein said pressing is applied by a pair of grounded substantially semicylindrical electrodes coaxial with said mandrel and having a diameter substantially equal to the outer diameter of said coil, and said electric field is applied between said mandrel and said electrodes by applying RF energy to said mandrel.

* * * * *